United States Patent
Sailor et al.

(10) Patent No.: US 8,852,447 B2
(45) Date of Patent: Oct. 7, 2014

(54) POROUS NANOSTRUCTURES AND METHODS INVOLVING THE SAME

(75) Inventors: Michael J. Sailor, La Jolla, CA (US); Gaurav Abbi, San Jose, CA (US); Boyce E. Collins, San Diego, CA (US); Keiki-Pua S. Dancil, Makawao, HI (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/590,825

(22) Filed: Aug. 21, 2012

(65) Prior Publication Data

US 2013/0217786 A1    Aug. 22, 2013

Related U.S. Application Data (62) Division of application No. 10/546,522, filed as application No. PCT/US2004/006880 on Mar. 5, 2004, now Pat. No. 8,274,643.

(60) Provisional application No. 60/452,265, filed on Mar. 5, 2003.

(51) Int. Cl.
| | |
|---|---|
| *B44C 1/22* | (2006.01) |
| *G01N 33/552* | (2006.01) |
| *C25F 3/14* | (2006.01) |
| *G01N 33/543* | (2006.01) |
| *A61K 9/00* | (2006.01) |
| *G01N 21/77* | (2006.01) |

(52) U.S. Cl.
CPC ............ *C25F 3/14* (2013.01); *G01N 33/552* (2013.01); *G01N 33/5438* (2013.01); *G01N 2021/7776* (2013.01); *G01N 2021/7773* (2013.01); *A61K 9/0097* (2013.01)

USPC ............ 216/2; 216/56; 438/745; 438/753; 205/640; 435/7.1; 257/E21.215

(58) Field of Classification Search
None
See application file for complete search history.

(56) References Cited

U.S. PATENT DOCUMENTS

| | | |
|---|---|---|
| 3,625,653 A | 12/1971 | Messing |
| 5,011,690 A | 4/1991 | Garvey et al. |
| 5,318,676 A | 6/1994 | Sailor et al. |
| 5,338,415 A | 8/1994 | Sailor et al. |
| 5,356,782 A | 10/1994 | Moorman et al. |
| 5,453,624 A | 9/1995 | Sailor et al. |
| 5,563,707 A | 10/1996 | Prass et al. |

(Continued)

FOREIGN PATENT DOCUMENTS

WO    WO 00/66190    11/2000

OTHER PUBLICATIONS

H. Arwin et al., "Protein Adsorption in Thin Porous Silicon Layers", Phys. Stat. Sol. (A), vol. 182, year 2000, pp. 515-519.*

(Continued)

*Primary Examiner* — Lan Vinh
*Assistant Examiner* — Jiong-Ping Lu
(74) *Attorney, Agent, or Firm* — Greer, Burns & Crain, Ltd.

(57) ABSTRACT

A method for simultaneously detecting and separating a target analyte such as a protein or other macromolecule that includes providing a porous silicon matrix on the silicon substrate, exposing the porous silicon matrix to an environment suspect of containing the target analyte, observing optical reflectivity of the porous silicon matrix; and correlating the changes in the silicon substrate to the target analyte.

16 Claims, 5 Drawing Sheets

(56) References Cited

U.S. PATENT DOCUMENTS

| | | | |
|---|---|---|---|
| 6,248,539 | B1 | 6/2001 | Ghadiri et al. |
| 6,312,888 | B1 | 11/2001 | Wong et al. |
| 6,720,177 | B2 | 4/2004 | Ghadiri et al. |
| 6,734,000 | B2 | 5/2004 | Chin et al. |
| 6,897,965 | B2 | 5/2005 | Ghadiri et al. |
| 7,042,570 | B2 | 5/2006 | Sailor et al. |
| 2001/0044119 | A1* | 11/2001 | Ghadiri et al. ............ 435/7.1 |
| 2002/0048531 | A1 | 4/2002 | Fonash et al. |
| 2002/0072116 | A1 | 6/2002 | Bhatia et al. |
| 2002/0074239 | A1 | 6/2002 | Berger et al. |
| 2002/0104762 | A1 | 8/2002 | Stonas et al. |
| 2002/0192680 | A1 | 12/2002 | Chan et al. |
| 2003/0146109 | A1 | 8/2003 | Sailor et al. |
| 2003/0231304 | A1 | 12/2003 | Chan et al. |
| 2004/0152135 | A1 | 8/2004 | Ghadiri et al. |
| 2004/0171143 | A1 | 9/2004 | Chin et al. |
| 2004/0244889 | A1 | 12/2004 | Sailor et al. |
| 2005/0009374 | A1 | 1/2005 | Gao et al. |
| 2005/0042764 | A1 | 2/2005 | Sailor et al. |
| 2005/0101026 | A1 | 5/2005 | Sailor et al. |
| 2006/0051872 | A1 | 3/2006 | Sailor et al. |
| 2006/0105043 | A1 | 5/2006 | Sailor et al. |
| 2006/0236436 | A1 | 10/2006 | Li et al. |
| 2006/0255008 | A1 | 11/2006 | Link et al. |
| 2007/0051815 | A1 | 3/2007 | Sailor et al. |
| 2007/0108465 | A1 | 5/2007 | Pacholski et al. |
| 2007/0148695 | A1 | 6/2007 | Sailor et al. |

OTHER PUBLICATIONS

A. Jashoff et al., "Macroporous p-Type Silicon Fabry-Perot Layers, Fabrication, Characterization, and Applications in Biosensing", J. Am. Chem. Soc. vol. 120, year 1998, pp. 12108-12116.*

W.R. Thurber et al., "Resistivity-Dopant Density Relationship for Boron-Doped Silicon", J. Electrochem Soc., vol. 127, year 1980, pp. 2291-2294.*

H. Arwin et al., "Protein Adsorption in Thin Porous Silicon Layers", Phys. Status Solidi A., vol. 182, 2000, pp. 515-520.

K.E. Bean, "Anisotropic Etching of Silicon", IEEE Transactions on Electron Devices, vol. Ed. 25, No. 10, 1978, pp. 1185-1193.

D. Bellet et al., "Controlled Drying: The Key to Better Quality Porous Semiconductors", Advanced Materials, vol. 10, 1998, pp. 487-490.

L. Bousse et al., "Zeta Potential Measurements of $Ta_2O_5$ and $SiO_2$ Thin Films", Journal of Colloid Interface Science, vol. 147, No. 1, 1991, pp. 22-32.

L.T. Canham et al., "Progress Towards Silicon Optoelectronics Using Porous Silicon Technology", Applied Surface Science., vol. 102, 1996, pp. 436-441.

L.T. Canham et al., "Derivatized Porous Silicon Mirrors: Implantable Optical Components with Slow Resorbability", Phys. Status Solidi A, vol. 182, 2000, p. 521-525.

S. Chan et al., "Porous Silicon Microcavities for Biosensing Applications", Phys. Status Solidi A, vol. 182, 2000, p. 541-546.

B.E. Collins et al., "Determining Protein Size Using an Electrochemically Machined Pore Gradient in Silicon", Advanced Functional Materials, vol. 12, No. 3, Mar. 2002, pp. 187-191.

C.L. Curtis et al., "Observation of Optical Cavity Modes in Photoluminescent Porous Silicon Films", J. Electrochem. Soc., vol. 140, Dec. 1993, pp. 3492-3494.

K.P.S. Dancil et al., "A Porous Silicon Optical Biosensor: Detection of Reversible Binding of IgG to a Protein A-Modified Surface", J. Am. Chem. Soc., vol. 121, 1999, pp. 7925-7930.

H. Foll et al., "A New View of Silicon Electrochemistry", Phys. Status Solidi A, vol. 182, 2000, pp. 7-16.

J. Gao et al., "Porous-Silicon Vapor Sensor Based on Laser Interferometry", Applied Physics Letters., vol. 77, No. 7, Aug. 7, 2000, pp. 901-903.

A. Janshoff et al, "Macroporous p-Type Silicon Fabry—Perot Layers. Fabrication, Characterization and Applications in Biosensing", J. Am. Chem. Soc., vol. 120, 1998, pp. 12108-12116.

R. Jedamzik et al., "Production of Functionality Graded Materials from Electrochemically Modified Carbon Preforms", J. Am. Ceram. Soc., vol. 83, No. 4, 2000, pp. 983-985.

N.M. Kalkhoran et al., "Optoelectronic Applications of Porous Polycrystalline Silicon", Appl. Phys. Lett, vol. 63, No. 19, Nov. 8, 1993, pp. 2661-2663.

V. Lehmann et al., "Formation Mechanism and Properties of Electrochemically Etched Trenches in n-Type Silicon", J. Electrochem. Soc., vol. 137, No. 2, Feb. 2, 1990, pp. 653-659.

V. Lehmann, "The Physics of Macropore Formation in Low Doped n-Type Silicon", J. Electrochem. Soc., vol. 140, No. 10, Oct. 1993, pp. 2836-2843.

V. Lehmann et al., "On the Morphology and the Electrochemical Formation Mechanism of Mesoporous Silicon", Materials Science & Engineering B, vol. 69-70, 2000, p. 11-22.

V. Lehmann et al., "Optical Shortpass Filters Based on Macroporous Silicon", Applied Physics Letters, vol. 78, No. 5, Jan. 29, 2001, pp. 589-591.

S. Létant, et al., "Molecular Identification by Time-Resolved Interferometry in a Porous Silicon Film", Advanced Materials, vol. 13, 2001, pp. 335-338.

V.S. Lin et al., "A Porous Silicon-Based Optical Interferometric Biosensor", Science, vol. 278, Oct. 31, 1997, pp. 840-843.

A.H. Mayne et al., "Biologically Interfaced Porous Silicon Devices", Phys. Status Solidi A., vol. 182, 2000, pp. 505-513.

T. Nakagawa et al., "Fabrication of Periodic Si Nanostructure by Controlled Anodization", Jpn. J. Appl. Phys., vol. 37, Pt. 1,No. 12B, 1998, pp. 7186-7189.

M.J. Sailor et al., "Surface Chemistry of Luminescent Silicon Nanocrystallites" Adv. Mater. 1997, vol. 9, No. 10, 1997, pp. 783-793.

P.V. Stevens et al., "Modification of Ultrafiltration Membrane with Gelatin Protein", Biotechnology and Bioengineering., vol. 57, 1998, Jan. 5, 1998, pp. 26-34.

A.M. Tinsley-Brown et al., "Tuning the Pore Size and Surface Chemistry of Porous Silicon for Immunoassays" Phys. Status Solidi A., vol. 182, 2000, pp. 547-553.

D. van Noort et al., "Monitoring Specific Interaction of Low Molecular Weight Biomolecules on Oxidized Porous Silicon Using Ellipsometry", Biosensors & Bioelectronics, vol. 13, Nol. 3-4, 1998, pp. 439-449.

M. V. Wolkin et al., "Porous Silicon Encapsulated Nematic Liquid Crystals for Electro-Optic Applications", Phys. Status Solidi A, vol. 182, 2000, pp. 573-578.

S. Zangooie et al., "Protein Adsorption in Thermally Oxidized Porous Silicon Layers", Thin Solid Films, vol. 313-314, 1998, pp. 825-830.

S. Zangooie et al., "Microstructural Control of Porous Silicon by Electrochemical Etching in Mixed HC1/HF Solutions", Applied Surface Science, vol. 136, 1998, pp. 123-130.

Curtis, C.L., et. al., "Observation of Optical Cavity Modes in Photoluminescent Porous Silicon Films", J. Electrochem. Soc., vol. 140, 1993, pp. 3492-3494.

Zangooie, S., et. al., "Microstructural Control of Porous Silicon by Electrochemical Etching in Mixed HC1/HF Solutions", Applied Surface Science, 136 (1998) pp. 123-130.

Collins, BE, et. al., "Molecular size estimation using reflective porous silicon thin films with porosity gradients." in: Parkhutik, V and L. Canham, eds., Porous Semiconductors—Science and Technology: Extended abstracts of the Second International Conference, Madrid, Spain, Mar. 12-17, 2000 (Alcoy, PSST 2000, 2000), pp. 280-281.

Karlsson, LM et al. Back-side etching. Journal of the Electrochemical Society. 2002. 149(12): C648-C652. Available electronically Oct. 29, 2002.

* cited by examiner

POROUS NANOSTRUCTURES AND METHODS INVOLVING THE SAME

REFERENCE TO RELATED APPLICATION AND PRIORITY CLAIM

The present application claims priority under 35 U.S.C. §120 and is a division of U.S. patent application Ser. No. 10/546,522, filed on Oct. 24, 2005, incorporated by reference herein, which was a US National Phase Application from PCT/US04/06880, which was filed on Mar. 5, 2004 and claims priority under 35 U.S.C. §119 of U.S. Provisional Application Ser. No. 60/452,265, which was filed on Mar. 5, 2003.

STATEMENT OF GOVERNMENT INTEREST

This invention was made with government support under Grant No. N6601-98-C-8514 awarded by the US Department of the Navy Space and Naval Warfare System Command. The government has certain rights in the invention.

FIELD

A field of the instant invention is sample analysis, e.g., detection and separation of an analyte. Another exemplary field of the invention is porous Si fabrication. Still another exemplary field of the invention is the use of porous Si templates for controlled drug delivery.

BACKGROUND

Separation and detection of an analyte, such as a macromolecule, protein, protein fragment, polymer, biomolecule, biopolymer, biological cell, a small molecule or other molecular complex has widespread application in fields such as genomics, proteomics, drug discovery, medical diagnostics, environmental sensing, pollution monitoring, detection of chemical or biological warfare agents, and industrial process monitoring. One common technique used to separate analytes such as proteins, polymers, biomolecules and other macromolecules based on size is size-exclusion chromatography (SEC). Analysis using SEC is usually performed by elution of the analyte solution of interest along the appropriate porous stationary phase and detection of the separated products at the end of the column using for example ultraviolet (UV) absorption, refractive index changes, or mass spectroscopy. However, the time scale associated with SEC experiments is such that analytes comprising weakly bound complexes typically cannot be characterized in this fashion because weakly bound complexes will typically dissociate and rather than characterizing the analyte, the constituent amino acids or other constituent molecules will be characterized. SEC is susceptible to other drawbacks, such as its complicated calibration, its slowness and inefficiency, and its rather large scale, which leads to a wasteful use of expensive, hazardous and environmentally troublesome solvents. SEC itself is a lengthy process, and since SEC only measures hydrodynamic volume, a further subsequent process is necessary to detect and identify the specific molecule, which unduly lengthens the procedure.

Conventional methods for fabricating Si nanostructures that may subsequently be used in separating and detecting applications have presented drawbacks as well, namely that pore size, configuration and distribution have been difficult to control, predict and reproduce. Reducing or eliminating these drawbacks has advantages in numerous applications as well. For example, in controlled release of a pharmaceutical, the drug of interest is usually infused in a porous material that slowly releases the drug at a rate that is therapeutically relevant. Many porous materials have been used, including porous Si, polymers such as poly(lactide), liposomes, and porous silica glasses. The release rates are dependent on many parameters, among which parameters is pore size in the host material. In some cases it is desirable to tailor the release characteristics to follow prescribed dose-time characteristics, and conventional methods have proven unsatisfactory in this respect.

SUMMARY OF THE INVENTION

The instant invention is related to a method for fabricating porous Si nanostructures and a method for using the porous Si nanostructures to separate and, in preferred embodiments of the invention, simultaneously detect a variety of target analytes, such as a macromolecule, protein, protein fragment, polymer, biomolecule, biopolymer, biological cell, a small molecule or other molecular complex in a nanocrystalline matrix. A preferred embodiment of the instant invention includes a method of forming a porous Si substrate for sensing a target analyte having a predetermined size and configuration that includes providing a silicon substrate and creating a predetermined pore configuration by electrochemically etching the silicon substrate with an asymmetric electrode configuration in the electrochemical cell that provides a predetermined current gradient.

Another preferred embodiment method of the invention includes providing a silicon substrate, creating a porous silicon matrix on the silicon substrate, exposing the porous silicon matrix to an environment suspect of containing the target analyte, observing optical changes in the silicon substrate, and correlating the changes in the silicon substrate to characteristics which are representative of the identity of the target analyte. Additionally, embodiments of the present invention provides a device and method to control pore release characteristics because it not only provides control of pore size, but also the invention provides controls the distribution of pore sizes in one monolithic material.

DETAILED DESCRIPTION OF THE PREFERRED EMBODIMENTS

Conventional methods of generating porous Si nanostructures that may then be used in separating and detecting analytes such as macromolecules, proteins, protein fragments, polymers, biopolymers, biomolecules, small molecules, biological cells or other molecular complexes, include inherent drawbacks, notably that conventional methods are slow and require several sequential steps in order to detect and separate a particular analyte. Use of porous silicon (Si) to separate and detect these analytes provides an advantageous alternative to conventional methods in that the porosity and pore size of Si may be readily tuned and configured to suit a particular application, and could be used in varying applications spanning biohazard and bioweapons detection, to in vivo detection of viral proteins. In addition, porous Si may be used the separate and detect analytes embodiments of the invention. Furthermore, porous Si has the added advantage of being conducive to being configured in a compact format, such as a chip, a wafer, or other types of thin film, making porous Si amenable to applications placing a premium on small size and transportability. Additionally, using Si as a matrix for detection and separation provides a faster method in that simultaneous detection and separation is possible, and its use is conducive to integration with other analytical tools, such as Matrix Assisted Laser Desorption Ionization, or MALDI. In further embodiments of the invention, porous Si is be configured to allow admission and controlled release of a relatively small drug.

Nanocrystalline porous Si films may be employed both as biosensors (for unlabeled proteins and deoxyribonucleic acid, or DNA) and as chromatography matrices, and as such, are useful in coupling the detection and separation processes as simultaneous events. The instant invention includes use of porous Si for the simultaneous detection and separation of analytes, including macromolecules, proteins, biomolecules and other molecular complexes, using a porous Si layer that has been electrochemically machined to present a range of pore sizes to an analyte solution.

While numerous analytes may be separated and detected using embodiments of the instant invention, for exemplary purposes, a test molecule, bovine serum albumin (BSA), will be discussed herein. The admittance of BSA in the porous Si film is preferably monitored using the optical interference technique to demonstrate the existence of a critical pore size, above which a characteristic change in the optical index of the film is detected. In addition, a critical relationship between surface charge and isoelectric point (pI, pH at which the molecule has no net charge) of the protein is monitored for purposes of separation and detection.

Porous Si films displaying a distribution of pore dimensions may preferably be generated by electrochemically etching Si in aqueous ethanolic HF using an asymmetric electrode configuration. The porous Si film may be nanomachined to have a predetermined configuration in that the median pore size and breadth of the size-distribution in the Si film may optionally be set by adjusting the HF concentration, current density, and position of the counter electrode relative to the Si electrode. Preferably, Si films with pore sizes in the range of a few nanometers are used as size-exclusion matrices, and are capable of performing an "on-chip" determination of macromolecule dimensions. Advantageously, embodiments of the instant invention allow formation of different pore sizes across an Si film during a single process.

Pore size variation may be configured specifically to a target analyte. For example pores having a diameter ranging from between 2 and 10 nanometers may be configured to allow admission and controlled release of a relatively small drug. Pores having a diameter ranging from 10 to 50 nanometers may be configured for separation of protein molecules, pores having a diameters ranging from 50 to 300 nanometers may be configured for separation of viral particles, and pores having diameters ranging from 500 nanometers to 5 microns may be configured to admit and separate bacterial cells.

More specifically, the chip or other Si film substrate may be exposed to an environment suspect of including a particular analyte, especially a protein, such as by being immersed in a suspect solution or by exposing the chip to air or vapors above a reactor. Exposure may include immersing the chip in the vapor, or simply flowing the vapor over the chip. Analysis of the exposed chip will reveal the size of the of the target analyte, by an examination of the reflectivity spectra. As an example, using the test molecule, BSA, optical reflectivity spectra of the thin porous Si films display distinctive shifts in the Fabry-Perot fringes in regions of the Si film where the pore dimensions are larger than a critical size, which is interpreted to be the characteristic dimensions of the protein. Gating of the protein in and out of the porous films is preferably achieved by adjustment of the solution pH below and above the pI (isoelectric point) value, respectively, though it can also be achieved by adjustment of a bias potential on the Si sample, or alternatively by changing the temperature of the sample. Further discrimination can also be achieved by addition of selective binding agents, such as antibodies, for the analyte.

Porous Si is a nanocrystalline matrix that may be formed on single crystal Si film, such as a chip, wafer, or other thin film in an electrochemical etch. Formation of porous Si involves the electrochemical oxidation of Si in a solution containing hydrofluoric acid (HF). The properties of the porous layer, such as pore size and porosity, are dependent on a number of factors, such as HF concentration, dopant type and density in the Si substrate, and current density used in the electrochemical etch. Exemplary dopants include boron, antimony, or phosphorus, with exemplary concentrations varying from between approximately $10^{22}$ cm$^{-3}$ and $10^{16}$ cm$^{-3}$. Similarly, exemplary current density may range from 1 microamp per cm$^2$ and 2 amp per cm$^2$.

A particular advantage of a formation method according to an exemplary embodiment is the ability to form reproducible porous Si micro- and nano-architectures, which has contributed to successful incorporation of these structures in biosensors and optoelectronic components. While methods of detection may vary to suit individual applications, a preferred detection modality is measurement of the Fabry-Perot fringes that result from optical interference between the top and bottom surfaces of the porous Si film. Thus, by monitoring changes in the refractive index of the Si film, volume and molecular weight of a target analyte may be readily identified.

Figure 1:
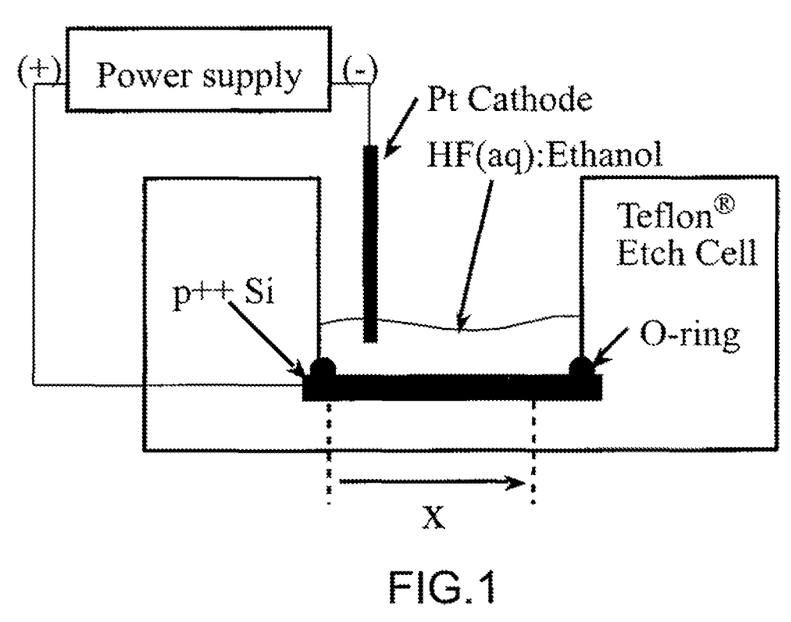
FIG. 1 is a schematic diagram of a preferred embodiment electrochemical cell and electrode arrangement used to generate pore gradients.

Preparation and Characterization of Porous Si Films Possessing Lateral Pore Gradients For purposes of the preferred embodiment, porous Si films containing a distribution or pore sizes may be electrochemically prepared using the asymmetric electrode configuration illustrated in FIG. 1. Turning therefore to FIG. 1 for exemplary purposes, a diameter of an O-ring is illustrated to be approximately 1.3 cm. A counter electrode is preferably placed ~1 mm from the Si working electrode surface and ~1 mm from the edge of the O-ring. The value of x used in FIG. 1 refers to a distance from a point on the O-ring edge closest to a Pt counter electrode to a position on the Si surface as illustrated, and the Pt counter electrode is disposed at approximately x=1 mm. In this arrangement, a potential at the Si electrode-solution interface varies as a function of distance from the Pt counter electrode due to solution resistance, leading to a decrease in current density as the distance from the counter electrode increases. Pores ranging in size from 2-1500 nm may be obtained in highly boron-doped Si substrates (p**) by varying such factors as the current density, and that pore size may also determined by the ratio of aqueous HF/ethanol used.

The asymmetric electrode configuration provides a current density gradient across the wafer that results in a distinct and reproducible variation in the size of the pores. This method is particularly advantageous in that it quickly prepares a material that has a predetermined range of pore sizes. Conventional methods for preparing materials containing a range of pore or void sizes are cumbersome, unduly expensive and relatively slow. In contrast, embodiments of the instant invention provide for preparation of a porous sample having a distribution of pore sizes in the same monolithic substrate simultaneously, whereas in previous methods separate steps would need to be undertaken to generate the same distribution of pore sizes. In addition, a center and breadth of this pore size distribution can be controlled. This has been demonstrated experimentally. More specifically, to demonstrate the instant invention, three circular film samples of porous Si may be prepared in separate experiments wherein an HF(aq)/ethanol ratio in the electrolyte used to prepare these samples is varied between 1:1, 1:2, and 1:3, respectively and each circular sample is configured to be approximately 1.2 cm in diameter. By applying a current density of 115 mA/cm2 for 8 seconds to each of the three crystalline silicon samples, each of the resulting porous samples contains a distribution of pore sizes. Tapping-mode atomic force images reveal an approximately linear distribution of pore sizes in all three samples, and the maximum pore size, minimum pore size, and center of the size distribution is different for all three samples For a given electrode geometry, the properties of the Si pore gradient film may further be varied by varying the electrolyte composition. For example, almost no electropolished region is observed on the Si sample that was etched in HF(aq)/EtOH=3:1 solution, and the range of pore sizes (as determined from Atomic Force Microscopy, or AFM, measurements, not included) is less pronounced than in samples etched in HF(aq)/EtOH=1:1 and 2:1, respectively. In HF(aq)/EtOH=2:1 solutions, a film with a wider range of pore sizes is formed. Some of the porous film directly beneath the electrode position generally peels upon drying, but AFM measurements on the intact film reveals pore diameters ranging from ~600 nm adjacent to the peeled spot to <10-20 nm (AFM probe tip limited features) about 7 mm from the original counter electrode position.

Thickness of the Porous Films

Figure 3A:
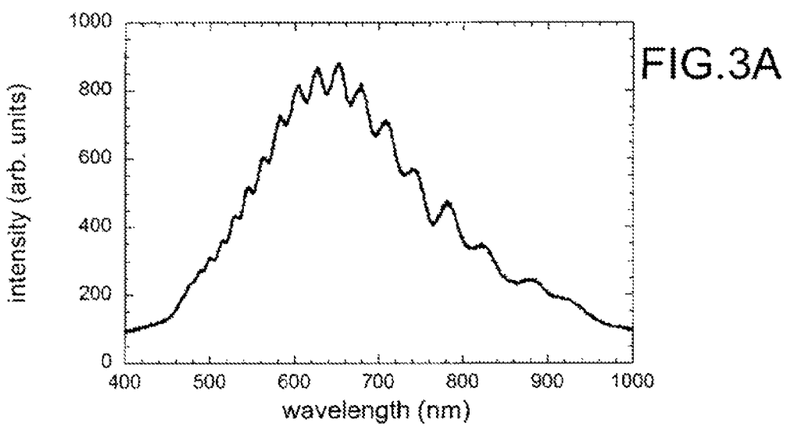
FIGS. 3A-3C are graphs illustrating the optical reflectance spectra taken from three different points (0.3 mm$^2$) on a porous Si wafer containing a pore gradient, showing the variation in the Fabry-Perot fringes along the length of a sample.
Figure 3B:
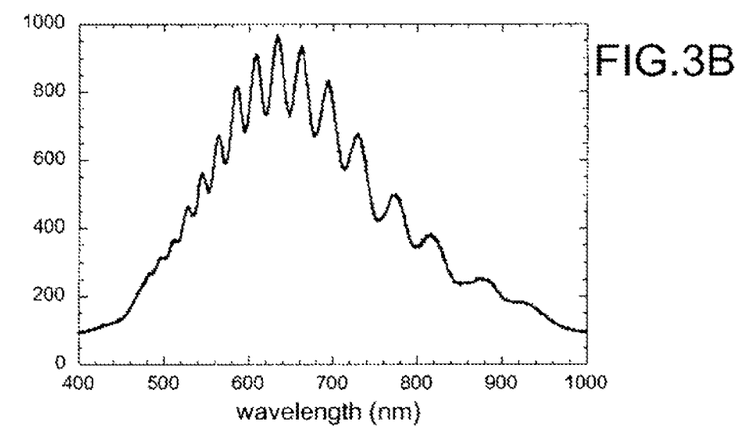
Figure 3C:
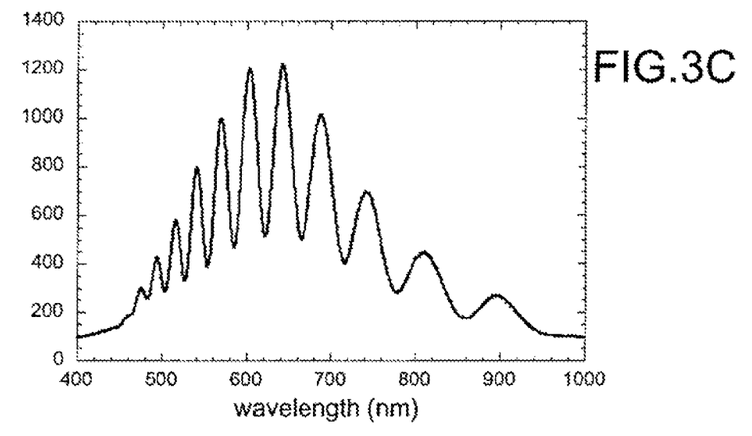

Profilometry measurements reveal that the thickness of the porous Si layer varies as a function of distance from the counter electrode, as illustrated in FIG. 3. The counter electrode was directly above the Si film at x=1.5 mm. Film thickness was measured by profilometry of the Si substrates after removal of the porous layer. In the exemplary embodiment, the etch conditions were as follows: 115 mA/cm$^2$, 90 seconds, HF(aq)/EtOH=1.5:1. To obtain the film thickness data the porous Si was removed by treatment with a basic solution (KOH/H$_2$O/isopropanol=5:16:4 by volume) for about 10 seconds. A similar depth profile was observed for all of the etch conditions employed and varied only moderately as a function of electrolyte composition. The films are generally thickest at the point directly under the counter electrode, consistent with that being the position of highest current density. The Si dissolution rate and hence the rate of film growth is directly proportional to the current density.

Figure 2:
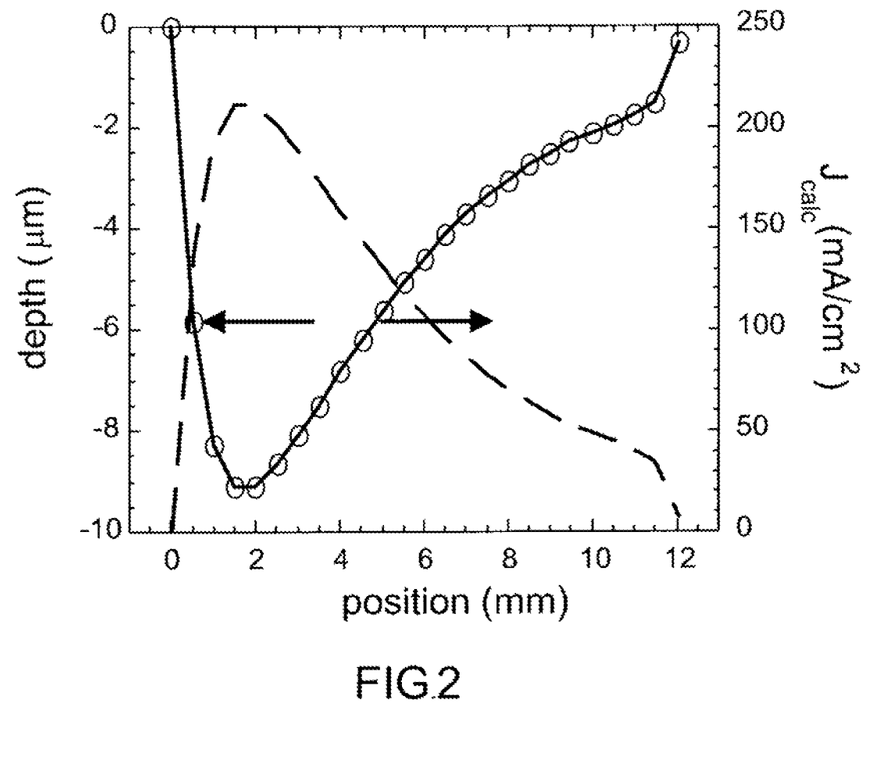
FIG. 2 is a graph illustrating the thickness of the porous Si film as a function of distance from the counter electrode (O) compared to the calculated current density (dashed line)

Thus, the profilometry data provide an indirect measure of the current density profile. The current density profile for the etch an also be estimated by applying Ohm's law to the electrode configuration and using reasonable values for the solution resistance, as illustrated in FIG. 2. For the electrochemical cell used in this embodiment, the current density varies from a value of ~200 mA/cm$^2$ directly under the electrode to less than ~50 mA/cm$^2$ at the far edge. Thus the porosity and depth variations observed in FIG. 2 are consistent with a current density variation that results from ohmic (IR, current-resistance voltage) drop in the solution.

Measurement of Fabry-Perot Fringes form the Porous Si Films

In regions of the film where the pore dimensions are too small to effectively scatter light, optical interference occurs between the air/porous Si and the porous Si/bulk Si. The reflection spectra of these films are described by the Fabry-Perot relationship and appear as a series of reflectivity maxima, as illustrated in FIG. 3. A wavelength of maximum constructive interference for the mth order fringe in a film of thickness L and refractive index n is given by the following equation:

$$m\lambda = 2nL$$

The quantity 2nL is herein referred to as the effective optical thickness (EOT). A change in the refractive index (n) that occurs upon introduction of molecular adsorbates, which are preferably the analyte for the particular application, in the porous Si film results in a shift in the optical fringes, which has been measured with a high sensitivity using either a spectrometer with a white light source, or a photodiode with a laser source.

Spatially resolved spectra were obtained using a microscope objective as a collection optic with a spatial resolution of approximately 0.3 mm$^2$. The spectra (taken in air) were obtained from spots on the Si wafer at approximately 2 mm (A), 5 mm (B), and 9 mm (C) from the counter electrode during preparation. Etch conditions were 115 mA/cm$^2$ for 90 seconds, 3:1 HF(aq)/EtOH electrolyte. FIG. 3 illustrates representative spectra from three points on a chip. As illustrated in FIG. 3, the spacing of the Fabry-Perot spectra obtained from samples that contain pore gradients vary across the length of the porous film because of variations in both depth and porosity. The variation in fidelity is ascribed to changes in refractive index contrast at the porous Si/air and porous Si/crystalline Si interfaces. The corresponding change in EOT is obtained from the Fourier transform of the intensity vs. frequency plot of the reflectivity spectrum (applying a Hanning window function to eliminate edge artifacts.).

Impregnation of biomolecules into a porous Si Fabry-Perot layer results in an increase in EOT because a certain volume of the thin film once occupied by the aqueous buffer solution is now occupied by the biomolecule, which has a larger index of refraction (e.g., $n_{buffer}$=1.33, $n_{protein}$=1.42). A film containing a range of pore diameters is expected to exhibit a change in EOT upon exposure to an analyte only in the regions of the film containing pores that are large enough to admit the analyte. In the present work, BSA was used as a probe analyte. BSA has an average molecular weight of 68 kD with its isolectric point at ph 5.

Figure 4A:
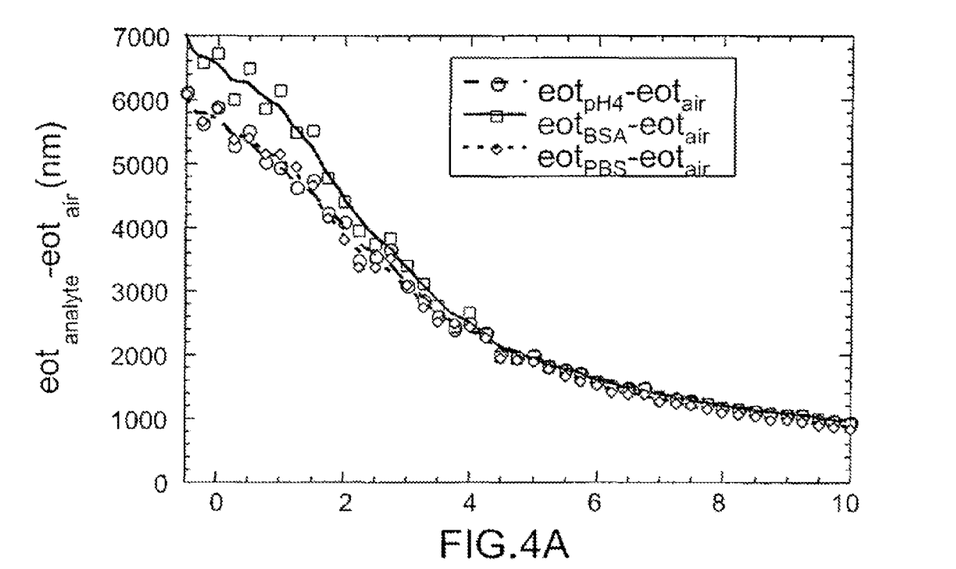
FIGS. 4A and 4B are graphs plotting admission or exclusion of BSA into the pores of a porous Si film as a function of the pore size.
Figure 4B:
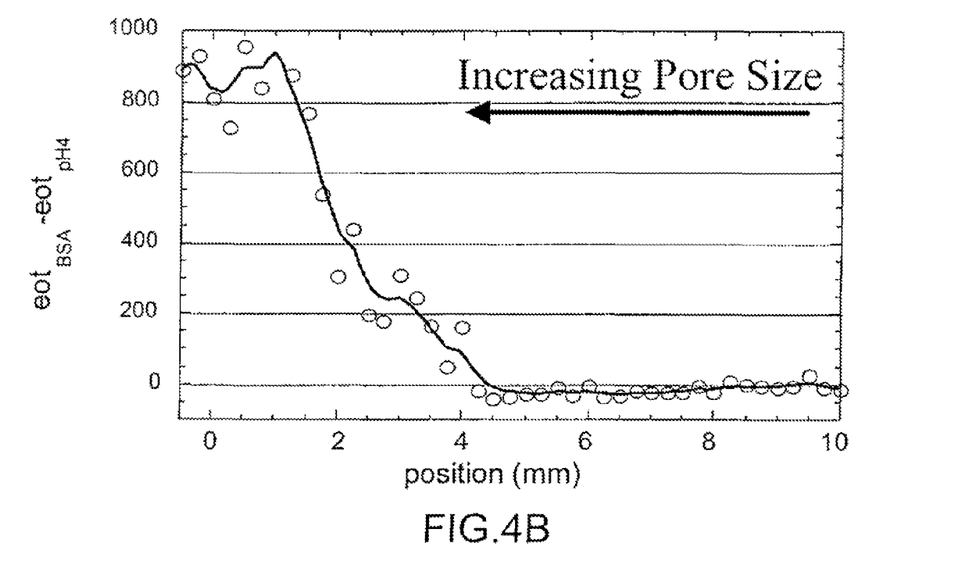

The data illustrated in FIGS. 4A and 4B represent the difference between the value of EOT measured in a given eluent and the EOT value measured in air, as a function of position (x) along the porous Si gradient. In both FIGS. 4A and 4B, the largest pores in the gradient are at position 0 mm, and the smallest are at position 10 mm. Each measurement was made as a function of position on the pore gradient wafer, and is relative to the edge of the wafer that was closest to the Pt counter electrode used in the etch. FIG. 4A specifically illustrates EOT measurement in the presence of pH 4 buffer (O), BSA in pH 4 buffer (⌵), and pH 7.2 PBS buffer (◊), relative to the measurement in air at the corresponding position. FIG. 4A specifically illustrates the difference between the two curves representing BSA in pH 4 solution (ـف in FIG. 4A) and pure buffer (pH 4) solution (O in FIG. 4A). The data indicate that BSA is admitted into the pores residing at positions between 0 and 4 mm from the film edge; at positions between 4 and 10 mm the pores are too small and BSA is excluded. Lines are included as a guide to the eye.

The positive change in EOT ($\Delta$EOT) values for all three solutions (pH 4 buffer, BSA in pH 4 buffer, and pH 7.2 phosphate buffered saline, PBS, buffer) demonstrate that the film is porous throughout its length. The change in EOT tends to be largest near x=0 (edge closest to the counter electrode position) for all solutions because the film is thickest and has the highest porosity at this point, resulting in the largest changes in EOT relative to air. FIG. 4B illustrates the difference observed in the chip with and without added BSA, obtained by subtracting the BSA (in pH 4 buffer) curve from the pH 4 buffer curve of FIG. 4A. Introduction of the BSA results in an increase in the relative values of EOT in the region of the chip between 0 and 4 mm. Thus, the region of the porous Si film at $0<x<4$ mm is interpreted to be the region in the gradient in which the pore size is large enough to allow entry of the BSA molecule. The response tapers off in the region $1<x<4$ mm, and no relative change is seen for BSA at $x>5$ mm, where the pores are presumably too small to admit BSA into the film.

2.5 pH-Gated Admission Experiments

Oxidation converts the porous Si hydride-terminated surface into an oxide that is negatively charged even at moderately low pH values. In contrast, the charge on the BSA molecule can be changed by appropriate adjustment of the pH. Thus the electrostatic interaction between the $SiO_2$-covered pore surface and the protein can be varied, allowing the separation of molecules based on their $pK_a$ values. The isoelectric point of BSA is approximately 5. Thus, at solution pH values above 5, the protein is negatively charged and below pH 5 the molecule is positively charged, due to $pK_a$ values of the constituent amino acid residues. In the size-exclusion experiments illustrated in FIG. 5, the pH of the system was maintained at 4, where the oxidized porous Si sample is expected to have a net negative charge and BSA is expected to have a net positive charge. However, if the pH is raised such that the protein becomes negatively charged, the biomolecule can be excluded from the porous silicon matrix.

Figure 5:
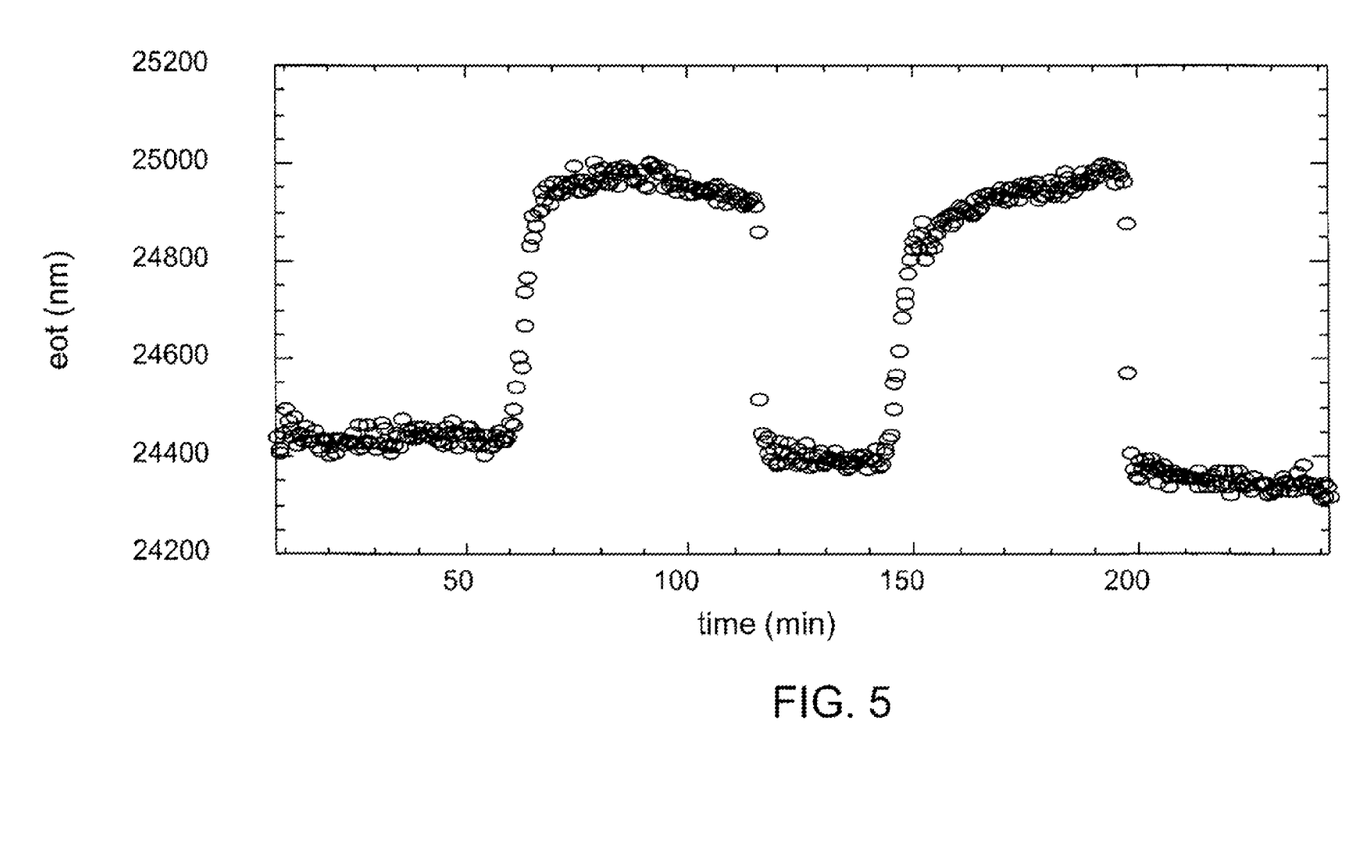
FIG. 5 is a graph plotting EOT versus time showing the adsorption and desorption of BSA into the porous film upon adjustment of the solution pH.

The result of adjusting the solution pH is demonstrated in FIG. 5. The sample used in this embodiment had pores that were large enough to accommodate BSA protein at pH 4. At time=0 (A in FIG. 6), aqueous PBS buffer (pH 7.2) is introduced into the flow cell. At point B, a solution of BSA in PBS buffer is added to the eluent stream. No change is observed in the EOT value, indicating that at this pH no protein is admitted to the pores. The flow cell is flushed with pure PBS buffer solution at pH 7.2 to remove residual BSA (C), and the buffer solution is then changed to potassium biphthalate buffer at pH 4 (D). Once the pH of the solution is lowered to the point where BSA has a net positive charge, BSA is introduced (E) and the value of EOT is observed to increase, corresponding to the admission of the protein into the porous silicon matrix. At point F, the solution is changed back to pure potassium biphthalate buffer (pH 4) containing no BSA. After this point the value of EOT is observed to gradually decrease, indicating that the protein trapped in the porous silicon matrix is slowly diffusing out. At point G, the PBS buffer solution is introduced, resulting in a rapid drop in the EOT value as the remaining BSA diffuses out of the pores. Desorption of BSA is strongly promoted in the pH 7.2 PBS buffer solution, presumably because the negatively charged protein is repelled by the negatively charged Si oxide surface. The reproducibility of the process may be probed in a second run, where BSA in pH 4 buffer is reintroduced (H) and subsequently removed with a PBS buffer rinse (I). Significant improvements in surface stability have been achieved by appropriate chemical modification of the porous Si surface, such as thermal hydrosilylation, photochemical hydrosilylation, or electrochemical grafting of species to the porous Si surface by means of Si—C bonded linkages. Notably, no BSA adsorption is observed when BSA is introduced in a pH 7.2 PBS buffer solution (FIG. 5, point B), and that no significant change in the EOT value is observed when the pH of the solution is changed from 4 to 7.2 in the absence of the protein (FIGS. 4A, 4B and 5D).

Porous Si films can be prepared that contain a controlled distribution of pore sizes using anisotropic etching conditions. The inhomogeneous etch results in a porous Si film having pore diameters that vary laterally and span a range of sizes from <10 nm to >500 nm. As illustrated in the drawings, the simultaneous separation and detection of a protein in a nanomachined Si matrix is achieved, as is gating of the response by adjustment of pH below and above the isoelectric point of the protein. This provides an additional means of analyte separation and identification. Thus, the instant invention simultaneously detects and separates the target analyte, which may then be subjected to further analysis. Embodiments of the instant invention are especially advantageous for determination of protein size and for the detection of weakly-bound complexes. Additionally, the ability to controllably trap and release analytes such as proteins may be useful for drug delivery applications, as porous Si has been shown to be biocompatible and readily bio-resorbable. More specifically, the porous Si film may be configured to have a predetermined porosity and predetermined pore size such that a specific drug having a specific molecular weight and a specific volume takes a predictably specific time to enter into and subsequently be released from a pore. In this manner, the specific drug may be time released in vivo.

More specifically, the porous Si film may be configured to have a range of pore sizes that promote a predetermined release profile, defined as the moles of drug released from the porous Si film versus time. The particular drug used in the instant embodiment may include anticancer drugs, chronic pain medication, anti-inflammatory drug such as dexamethasone, an anti-coagulant, an anti-rejection drug such as rapamycin (which is used in coronary artery stents to inhibit restenosis). The porous Si film, and therefore the drug, may be introduced through a variety of mechanisms, including transdermally, via intramuscular injection, intravenously, surgically implanted, through the throat or lungs, or orally ingested.

Another particular application of the instant invention involves proteomics where a solution may contain a complex mixture of proteins, but wherein it is desirable to isolate or purify a single protein within the mixture. For example, of particular interest are proteins that are produced by an undesirable genetic mutation, proteins that act as markers, or indicators, of a specific disease state, or proteins which currently have no known function but may be key in the future diagnosis or treatment of a disease. Once the mixture is subjected to the detection and separation processes of the instant invention, the target protein could then subsequently be subjected to processing in a MALDI instrument to refine identification of the molecule on the basis of high resolution mass spectrometry.

While various embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the following claims.

What is claimed is:

1. A method for forming a porous silicon matrix with a lateral pore gradient including an approximately linear distribution of pore sizes, comprising:
    placing a silicon substrate in an etching solution;
    disposing one end of a counter electrode in the etching solution at a distance from a surface or surface portion of the silicon substrate to be etched, the one end of the counter electrode being aligned proximate an edge of the surface or surface portion of the silicon substrate to be etched and an opposite end of the counter electrode being distant from the surface or surface portion of the substrate and the edge of the surface or surface portion; and
    applying power potential between the silicon surface and the counter electrode to create an etching current density gradient across the silicon substrate for a period of time to create the approximately linear distribution of pore sizes across the silicon surface.

2. The method of claim 1 wherein said disposing and applying create a predetermined pore configuration to correspond to a size and configuration of a target analyte.

3. The method of claim 1 wherein said disposing and applying are conducted to create pores having diameters ranging in size from between 2 and 10 nanometers to allow admission and controlled release of a small drug.

4. The method of claim 1 wherein said disposing and applying are conducted to create pores having diameters ranging in size from between 10 and 50 nanometers for separation of protein molecules.

5. The method of claim 1 wherein said disposing and applying are conducted to create pores having diameters ranging in size from between 50 and 300 nanometers for separation of viral particles.

6. The method of claim 1 wherein said disposing and applying are conducted to create pores having diameters ranging in size from between 500 nanometers and 5 microns to admit and separate bacterial cells.

7. The method of claim 1 wherein said silicon substrate that contains a dopant selected from the group consisting of boron, antimony, or phosphorus.

8. The method of claim 7 wherein the dopant has a dopant density from approximately $10^{22}$ cm$^{-3}$ and $10^{16}$ cm$^{-3}$.

9. The method of claim 1 wherein said applying power applies current to said substrate having a density ranging from 1 microamp per cm$^2$ and 2 amp per cm2.

10. The method of claim 1, wherein the etching solution comprises HF(aq)/EtOH in a volumetric ratio of between about 1:1 and 2:1.

11. The method of claim 1, wherein the approximately linear distribution of pore sizes has a predetermined range of pore sizes.

12. The method of claim 1, wherein the approximately linear distribution of pores sizes has a predetermined center.

13. The method of claim 1, wherein the counter electrode is substantially perpendicular to the surface or surface portion.

14. A method of forming porous silicon that selectively admit a target analyte having a predetermined isolectric point, said method comprising:
    providing a silicon substrate;
    electrochemically etching the silicon substrate to form a porous silicon matrix;
    oxidizing the porous silicon matrix:
    stabilizing the porous silicon matrix with chemical treatment;
    exposing the porous silicon matrix to the target analyte; and
    gating admission of the target analyte protein in and out of the porous silicon matrix by altering a pH of an analyte matrix either above or below the isoelectric point of the target analyte protein.

15. The method of claim 14 further comprising increasing the solution pH to be at least slightly greater than the isoelectric point of the target analyte protein to prevent admission of the target analyte in the porous silicon matrix.

16. The method of claim 14 further comprising decreasing the solution pH to be at least slightly less than the isoelectric point of the target analyte to promote admission of the target analyte in the porous silicon matrix.

* * * * *

UNITED STATES PATENT AND TRADEMARK OFFICE
CERTIFICATE OF CORRECTION

PATENT NO. : 8,852,447 B2  Page 1 of 1
APPLICATION NO. : 13/590825
DATED : October 7, 2014
INVENTOR(S) : Sailor It is certified that error appears in the above-identified patent and that said Letters Patent is hereby corrected as shown below:

On the Title Page:

Item (56):

Col. 2, lines 57-59

Delete "Zangooie. S., et al., "Microstructural Control of Porous Silicon by Electrochemical Etching in Mixed HC1/HF Solutions", Applied Surface Science, 136 (1998) pp. 123-130.".

In the Specification:

| | |
|---|---|
| Col. 2, line 38 | Delete "provides" and insert --provide-- therefor. |
| Col. 2, line 40 | Delete "provides controls" and insert --provides control of-- therefor. |
| Col. 5, line 66 | Delete "an" and insert --can-- therefor. |
| Col. 6, line 55 | Delete "kD" and insert --kDa-- therefor. |
| Col. 6, line 67 | Delete "ﻓ" and insert --□-- therefor. |
| Col. 7, line 3 | Delete "ﻓ" and insert --□-- therefor. |

In the Claims:

| | |
|---|---|
| Col. 10, line 3, Claim 7 | After "substrate" delete "that". |
| Col. 10, line 10, Claim 9 | Delete "cm2" and insert --$cm^2$-- therefor. |

Signed and Sealed this
Twenty-third Day of June, 2015

Michelle K. Lee
*Director of the United States Patent and Trademark Office*